(12) United States Patent
Hubner-Parajsz et al.

(10) Patent No.: US 6,630,350 B1
(45) Date of Patent: Oct. 7, 2003

(54) MONOCLONAL ANTIBODIES AGAINST A HUMAN ACT AND SERINE PROTEASE COMPLEX

(75) Inventors: Christa Hubner-Parajsz, Tutzing (DE); Hartmut Schetters, Penzberg (DE); Rosemarie Kientsch-Engel, Feldafing (DE); Thomas Meier, Munich (DE); Martin Kaufmann, Weilheim (DE); Andreas Gallusser, Penzberg (DE); Rolf Deeg, Bernried (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/284,128

(22) PCT Filed: Oct. 9, 1997

(86) PCT No.: PCT/EP97/05556

§ 371 (c)(1),
(2), (4) Date: Sep. 3, 1999

(87) PCT Pub. No.: WO98/15580

PCT Pub. Date: Apr. 16, 1998

(30) Foreign Application Priority Data

Oct. 6, 1996 (DE) ......................................... 196 41 560

(51) Int. Cl.[7] .............................................. C12H 15/85
(52) U.S. Cl. ........................ 435/326; 435/7.1; 435/325; 530/387.1; 530/403
(58) Field of Search .................... 435/7.1, 325, 326; 530/387.1, 403

(56) References Cited

U.S. PATENT DOCUMENTS

| 5,501,983 A | | 3/1996 | Lilja et al. .................. 436/518 |
| 5,928,878 A | * | 7/1999 | Allard et al. ................. 435/7.1 |

FOREIGN PATENT DOCUMENTS

| DE | 43 22 342 | 2/1995 | |
| EP | 0 635 575 | 1/1995 | |
| WO | WO 92/01936 | 7/1991 | |
| WO | WO 92/18381 | 7/1995 | |
| WO | WO 98/22509 | 5/1998 | ........... C07K/16/40 |

OTHER PUBLICATIONS

Finlay et al. "Development of Monoclonal Antibodies Specific for Human Glandular Kallikrein (hK2): Development of a Dual Antibody Immunoassay for hK2 with Negligible prostate–Specific Antigen Cross–Reactivity", Urology 51(5): 804–809, 1998.

Perlmutter et al. "Endocytosis and Degradation of $\alpha_1$ –Antitrypsin–Protease Complexes Is Mediated by the Serpin–Enzyme Complex (SEC) Receptor", J. of Biol. Chem., 265 (28), 16716–16716, 1990.

Villoutreix et al. "Structural investigation of the alpha–1–antichymotrypsin: prostate–specific antigen complex by comparative model building", *Protein Science* (1996), 5:836–851.

Cell Biology: Perlmutter et al. "Identification of a serpin–enzyme complex receptor on human hepatoma cells and human monocytes", *Proc. Natl. Acad. Sci.* USA 97 (1990) pp. 3753–3757.

Wu et al. "Correlation of Serum Concentrations of PSA–ACT Complex with Total PSA in Random and Serial Specimens From Patients with BPH and Prostate Cancer", Journal of Clinical Laboratory Analysis 9:15–24 (1995).

Joslin et al. "Cross–Competition for Binding of Alpha1–Antitrypsin (Alpha1AT)–Elastase Complexes to the Serpin–Enzyme Complex Receptor by Other Serpin–Enzyme Complexes and by Proteolytically Modified Alpha1 AT" Journal of Biological Chemistry, Bd. 268, Nr. 3, (1993).

\* cited by examiner

*Primary Examiner*—Susan Ungar
*Assistant Examiner*—Minh-Tam Davis
(74) *Attorney, Agent, or Firm*—Jill L. Woodburn; Marilyn L. Amick

(57) ABSTRACT

The invention concerns monoclonal antibodies against a complex of human ACT and a serine protease, preferably against a ACT-PSA, which have essentially no cross-reactivity with free, non-complexed human ACT and with free, non-complexed PSA, as well as diagnostic test methods for detecting serine protease-ACT complexes, in particular PSA-ACT, using these monoclonal antibodies.

1 Claim, 1 Drawing Sheet

MONOCLONAL ANTIBODIES AGAINST A HUMAN ACT AND SERINE PROTEASE COMPLEX

CROSS-REFERENCE TO RELATED APPLICATIONS

This application claims priority under 35 U.S.C. §119 to International Patent Application No. PCT/EP97/05556, International Filing Date Oct. 9, 1997 and German Application Serial No. 196 41 560.8 filed Oct. 9, 1996.

BACKGROUND AND SUMMARY OF THE INVENTION

The present invention concerns monoclonal antibodies (MAB) which specifically bind a complex of α1-antichymotrypsin (ACT) and a serine protease, in particular prostate-specific antigen (PSA) and have essentially no cross-reactivity with non-complexed ACT and non-complexed serine proteases. These monoclonal antibodies can be used to detect ACT-serine-protease complexes and in particular to detect PSA-ACT.

The prostate-specific antigen is a glycoprotein with a molecular weight of 33 kDa. It is formed in the prostate epithelial cells and is a component of seminal fluid. PSA has the enzymatic activity of a neutral serine protease.

The main function of PSA is to cleave the seminogelins I and II and fibronectin that are gel-like proteins which, as the main component of the ejaculate, block the mobility of the sperm. PSA liquefies the seminal coagulum by hydrolysing these proteins and thus enables the sperm mobility.

Enzymatically active PSA is inactivated in the serum by various inhibitors so-called serpins (=serine protease inhibitors), by the formation of covalent complexes. Most of the immunologically detectable PSA is bound in the serum to α1-antichymotrypsin (60–95%). Further complexes are formed with α2-macroglobulin, α1-antitrypsin, inter-α-trypsin inhibitor and protein C inhibitor. In addition an enzymatically inactive PSA also occurs which no longer complexes with serpins.

α1-antichymotrypsin is a glycoprotein with a molecular weight of ca. 69 kDa and a carbohydrate moiety. ACT plays an important role in the control of inflammations as one of the main inhibitors in the acute phase. ACT also forms complexes with chymotrypsin, cathepsin G and glandular kallikrein hK2. ACT is present in human serum in a 10,000-fold higher concentration than PSA (on a molar basis).

Apart from free PSA, the PSA-ACT complex is the main form of the immunologically detectable total PSA in serum. Prostate cancer leads in many cases to an increase in the serum PSA level. However, since slightly increased PSA serum values are also found in benign prostate hyperplasia, PSA is not a cancer-specific marker especially in the low concentration range. The previously available screening tests for the possible presence of a prostate carcinoma in a patient have always been tests for detecting total PSA. Since PSA normally occurs in very low concentrations in the serum of male persons, a so-called cut-off has to be defined for such a test. PSA values which are above this cut-off are evaluated as an indication for the presence of prostate carcinoma. Since the PSA concentration increases with increasing age of the patients, cut-off values of 4 to 6 ng/ml have previously been used for the test for the detection of total PSA. As a result some patients which had a prostate carcinoma in the early stage were not detected in these screening tests.

Already in the Japanese unexamined laid-open patent application 62-46263 it was found that increased values of complexed PSA occurred in patients with a malignant prostate tumour compared to patients with benign prostate hyperplasia. In this unexamined laid-open patent application an immunoassay was described which detects using a combination of an antibody against γ-seminoprotein (γ-seminoprotein is identical with PSA; see Schaller et al., Eur. J. Biochem. 170, 1987, 111–120 and Nakamura, Cancer 74, 1994, 1655–1659) and an antibody against α1-antitrypsin.

A method for the detection of PSA-ACT is described in WO 92/01936 in which a combination of the antibody 2E9, which binds uncomplexed PSA and also binds PSA in the complex with ACT, and an antibody against ACT is used.

In addition there are diagnostic tests for the detection of free, non-complexed PSA and total PSA i.e. the sum of free and complexed PSA. All these tests contain antibodies which in the case of a detection of free PSA only recognize PSA in a non-complexed form or in the case of a detection of total PSA only recognize PSA in a complexed and free form.

The detection of ACT in a complexed form with serine proteinases and in particular the detection of PSA-ACT was, as described above, only previously possible with the aid of a sandwich test using two antibodies of which one of the antibodies was directed against PSA and the other antibody was directed against ACT. Since ACT occurs in human serum in a ca. 10,000-fold excess compared to PSA and thus the complex composed of PSA and ACT also occurs, it is not possible to rule out negative test interference by this high excess of ACT. In particular it is essential in these previously known tests for detecting PSA-ACT to include at least one wash step to remove excess ACT before adding the ACT-specific antibodies in the test procedure. Thus a one step test procedure which is desirable for many automated diagnostic tests is not possible.

Therefore the object of the present invention was to provide an improved test for the detection of PSA-serine proteases, in particular PSA-ACT which should if possible not have interference by the presence of high ACT concentrations in the serum and which allows a screening which is as sensitive as possible for the detection of a prostate carcinoma.

The object is achieved by a monoclonal antibody against a complex of human ACT and a serine protease which has essentially no cross-reactivity with free, non-complexed human ACT and free, non-complexed serine proteases.

In particular the object was achieved by an MAB against a complex of ACT and a serine protease which has essentially no cross-reactivity with free human ACT and free serine proteases and which has a substantially higher affinity and specificity for PSA-ACT than for other serine protease-ACT complexes in particular chymotrypsin-ACT and cathepsin-G-ACT.

The monoclonal antibody can be used in all tests familiar to a person skilled in the art for the detection of a protein. In a preferred test procedure using two antibodies (sandwich test) the test can be carried out in one step i.e. without an additional wash step to remove the excess ACT. This is a decisive improvement compared to the previously possible tests which all included a wash step to remove the excess ACT, especially for screening tests in which numerous samples have to be tested as rapidly as possible.

The monoclonal antibodies according to the invention against a complex of human ACT and a serine protease essentially have no cross-reactivity with free human ACT and free serine proteases. Essentially no cross-reactactivity is understood as a cross-reactivity which in a test for the detection of the ACT-serine protease complex does not result in an influence by free ACT or free serine protease. The level of cross-reactivity with individual components that can still be tolerated depends on the concentration at which these components can occur in human serum. Since ACT occurs in a very large excess, the cross-reactivity must be infinitesimal in this case i.e. substantially below 1%. It was not possible to detect any cross-reactivity of the monoclonal antibodies according to the invention using the available methods. The BIACORE® system from the Pharmacia company was used to detect the cross-reactactivity. Antibodies with an affinity constant of less than $10^5$ l/mol for the tested substances exhibited no significant binding and thus no detectable cross-reactactivity in this system.

The monoclonal antibodies according to the invention exhibited no cross-reactivity towards non-complexed PSA, chymotrypsin and cathepsin G in the BIAcore®. In order to check cross-reaction with all potentially interfering substances that occur in human serum, human serum was added in this case to the screening test. A human female serum was used so that no ACT-PSA complexes are present. The monoclonal antibodies according to the invention exhibited no detectable cross-reactivity with other components occurring in this serum.

Since PSA-ACT represents the most clinically relevant serine protease-ACT complex, the monoclonal antibodies according to the invention have in particular a higher affinity and specificity for PSA-ACT than for other serine protease-ACT complexes. The affinity for PSA-ACT is preferably at least 10-fold higher and particularly preferably 50-fold or higher. These specific monoclonal antibodies against PSA-ACT enable a one step test to be designed for the detection of PSA-ACT which has no or no clinically significant interference by non-complexed PSA and ACT.

The monoclonal antibodies according to the invention preferably have an affinity for PSA-ACT of at least $10^7$ l/mol, particularly preferably of at least $10^9$ l/mol. One of the monoclonal antibodies according to the invention was even found to have an affinity of $10^{10}$ l/mol which is unusually high for monoclonal antibodies. Such high affinity monoclonal antibodies against PSA-ACT are excellently suitable for one step tests in which there is usually a relatively short incubation of the sample with the monoclonal antibody. The binding of this high affinity monoclonal antibody to PSA-ACT occurs very rapidly.

The monoclonal antibodies according to the invention can belong to all possible Ig classes. The monoclonal antibodies preferably belong to the IgG1 class. Additional components such as binding partners for binding the antibody to a solid phase in heterogeneous immunoassays or for example labels such as enzymes etc. can be preferably coupled to IgG1 antibodies. The cleavage of antibody fragments is also unproblematic the IgG1 class.

The term monoclonal antibody according to the invention is understood as the complete antibody as well as all fragments thereof that are commonly used in immunological tests and other applications such as $F(ab')_2$ and Fab fragments. The term also includes antibodies that have been produced by modifying the monoclonal antibodies provided the antigen binding property has not been significantly affected. For example parts of the monoclonal antibodies which are usually produced in mice can be replaced by corresponding human antibody sequences by genetic engineering in order to minimize unspecific binding in the immunoassay. Methods for producing such chimeric monoclonal antibodies are known to a person skilled in the art for example Antibody Engineering from J. Mc Cafferty, H. R. Hoogenboom and D. J. Chiswell, The Practical Approach Series, Series Editor: B. D. Hames, Oxford University Press, 1996.

The monoclonal antibodies according to the invention can for example be produced from the cell lines MAK<PSA-ACT>M 4.6.374, MAK<PSA-ACT>M 4.3.2 and MAK<PSA-ACT>M 6.13.64 deposited on the 19.9.1996 at the DSM ("Deutsche Sammlung von Mikroorganismen und Zellkulturen GmbH, Mascheroder Weg 1b, D-38124 Braunschweig). (MAK<PSA-ACT>M 4.6.474=DSM ACC 2281; MAK<PSA-ACT>M 6.13.64=DSM ACC 2282; MAK<PSA-ACT>M 4.3.2=DSM ACC 2283).

The hybridoma cell lines MAK<PSA-ACT>M 4.6.374, MAK<PSA-ACT>M 6.13.64, and MAK<PSA-ACT>M 4.3.2 were each deposited on Sep. 19, 1996 at the International Depository Authority DSMZ-Deutsche Sammlung Von Mikroorganismen Und Zellkulturen Gmbh (German Collection of Microorganisms and Cell Cultures, Ltd. (DSMZ)), Mascheroder Weg. 1b, D-38124 Braunschweig Germany under Nos. DSM ACC2281, DSM ACC2282, and DSM ACC2283 respectively at the German Collection of Microorganisms and Cell Cultures Ltd. (DSMZ) in accordance with the provision of the Budapest Treaty.

The invention also concerns antibodies and preferably monoclonal antibodies which bind to serine protease-ACT complexes in an equivalent manner to the monoclonal antibodies 4.6.374, 4.3.2 and 6.13.64. Bind in an equivalent manner is understood to mean that these antibodies recognize the same epitope as the deposited monoclonal antibodies. This can for example be determined by multi-binding experiments on the BIACORE®.

The monoclonal antibodies according to the invention can be produced in a known manner by immunizing suitable experiment al animals with PSA-ACT of human origin and subsequently fusing the spleen cells of the immunized animals with myeloma cells. The yield of serine protease-ACT-specific monoclonal antibodies was, however, very low. It was possible to increase the yield of PSA-serine-protease-specific antibodies by exclusively using female experimental animals. Even in this case ca. 70% of the monoclonal antibodies still had a high cross-reactivity with ACT and ca. 30% had a high cross-reactivity with PSA. Well below 1% of the total antibodies obtained had the required specificity for the serine protease inhibitor complex or the PSA-ACT complex.

In addition to spleen cells as a lymphocyte source it is also possible to use PBL (peripheral blood lymphocytes) or lymph node cells of immunized animals (preferably of the mouse and rat).

Alternatively it is also possible to immortalize lymphocytes (PBL, spleen cells, lymph node cells) from human donors (such as prostate tumour patients, lactating women, patients with PSA-secreting cells/tissues) which have developed antibodies or auto-antibodies against PSA-ACT. Such anti-PSA-ACT producing lymphocytes can either be immortalized by fusion with a human myeloma line or by EBV (Epstein Barr virus) transformation to form antibody-producing hybridoma cells (Monoclonal Antibody and Immunosensor Technology, A. M. Campbell, Elsevier Publisher 1991; "Monoklonale Antikörper", J. H. Peters, H. Baumgarten, Springer Verlag 1990; Monoclonal Antibody Production Techniques and Applications, ed. Lawrence B. Schook, Marcel Dekker Publisher 1987).

A further subject matter of the invention is the use of the monoclonal antibodies according to the invention for the detection of serine protease-ACT complexes in particular of PSA-ACT in samples, preferably human samples such as for example plasma, serum, blood, seminal fluid, prostate fluid, seminal vesicle fluid, saliva, liquor, human milk, cysts, tissue homogenates, tissue sections, biopsy material.

Since the monoclonal antibodies according to the invention specifically recognize the complex of serine protease and human ACT whereby it can be assumed that all MABs according to the invention recognize an epitope which only occurs in this complex but not in free serine proteases and free human ACT, it is possible to use all common test configurations which are suitable for detecting a protein. Therefore a person skilled in the art is no longer limited, as was previously the case, exclusively to a two step sandwich assay which, moreover, had to include a wash step before incubation of the human ACT-specific antibody.

Hence the invention additionally concerns a method for determining a complex of human ACT and serine proteases by incubating the sample with at least one monoclonal antibody according to the invention. All common methods familiar to a person skilled in the art for the detection of a protein such as competitive tests based on the IEMA principle or direct tests such as sandwich tests are suitable. Apart from heterogeneous tests in which the assay components are coupled to a solid phase and the solid and liquid phase are separated, it is also possible to use homogeneous tests that are suitable for detecting a protein. Examples of this are nephelometric or turbidimetric tests such as latex agglutination tests or TINIA (turbidimetric inhibition immunoassays). Apart from so-called wet tests in which the test reagents are present in a liquid phase, it is also possible to use all common dry test formats that are suitable for the detection of a protein. In these dry tests or test strips the test components are applied to a carrier. Such dry tests are for example described in EP-A 0 186 799.

A further subject matter of the invention is a test for the detection of PSA-ACT by incubating the sample with a monoclonal antibody according to the invention which has a higher affinity for PSA-ACT than for other serine protease-ACT complexes. This MAB preferably has an at least 10-fold and particularly preferably an at least 50-fold higher affinity for PSA-ACT.

If a combination of several antibodies is used in the test of which one is a monoclonal antibody according to the invention, it is possible to design PSA-ACT-specific tests even if a monoclonal antibody is used which recognizes all serine protease-ACT complexes equally well. Therefore a subject matter of the invention is a method for determining PSA-ACT by incubating the sample with at least one monoclonal antibody according to the invention and one antibody which is directed against PSA. Such PSA-specific antibodies are known and have already been used since 1985 in diagnostic tests for the detection of PSA or γ-seminoprotein. The combination of these two antibodies enables the specific detection of PSA-ACT. In this conventional sandwich test it is of no consequence which of the two antibodies is present in the labelled form or bound to the solid phase.

Instead of the monoclonal antibody that is specific for the complex of ACT and a serine protease, in particular the ACT-PSA complex, it is also possible to use a receptor for PSA-ACT in combination with the antibody against PSA. PSA is a member of the kallikrein family, a protease group which has a high degree of mutual homology. They are bound by inhibitors, the so-called serpins (serine protease inhibitors), which include ACT. These PSA-serpin complexes have an epitope, a so-called neo-epitope, which is not present on the free inhibitors which have bound no protease. These PSA-ACT complexes or in general the kallikrein-serpin complexes are eliminated from the blood circulation by means of receptors which recognize this neo epitope. The neo epitope is described for example in Perlmutter et al., J. Biol. Chem. 265, No. 28, 16713–16716, 1990; Perlmutter et al., Proc. Natl. Acad. Sci. USA, 87, 3753–3757, 1990 and Joslin et al., J. Biol. Chem. 268, No. 3, 1886–1893, 1993. The receptors for PSA-ACT and kallikrein-serpins were detected in Hep G2 cells and can be isolated from these (Joslin et al. 1993). Hence a further subject matter of the invention is a method for determining PSA-ACT by incubating the sample with a receptor for PSA-ACT which binds the neo epitope described in more detail above, and with an antibody which is preferably a monoclonal antibody directed against PSA. In this case it is of no consequence whether the receptor or the antibody are present in a labelled form or bound to the solid phase.

DETAILED DESCRIPTION OF THE INVENTION

Figure 1:
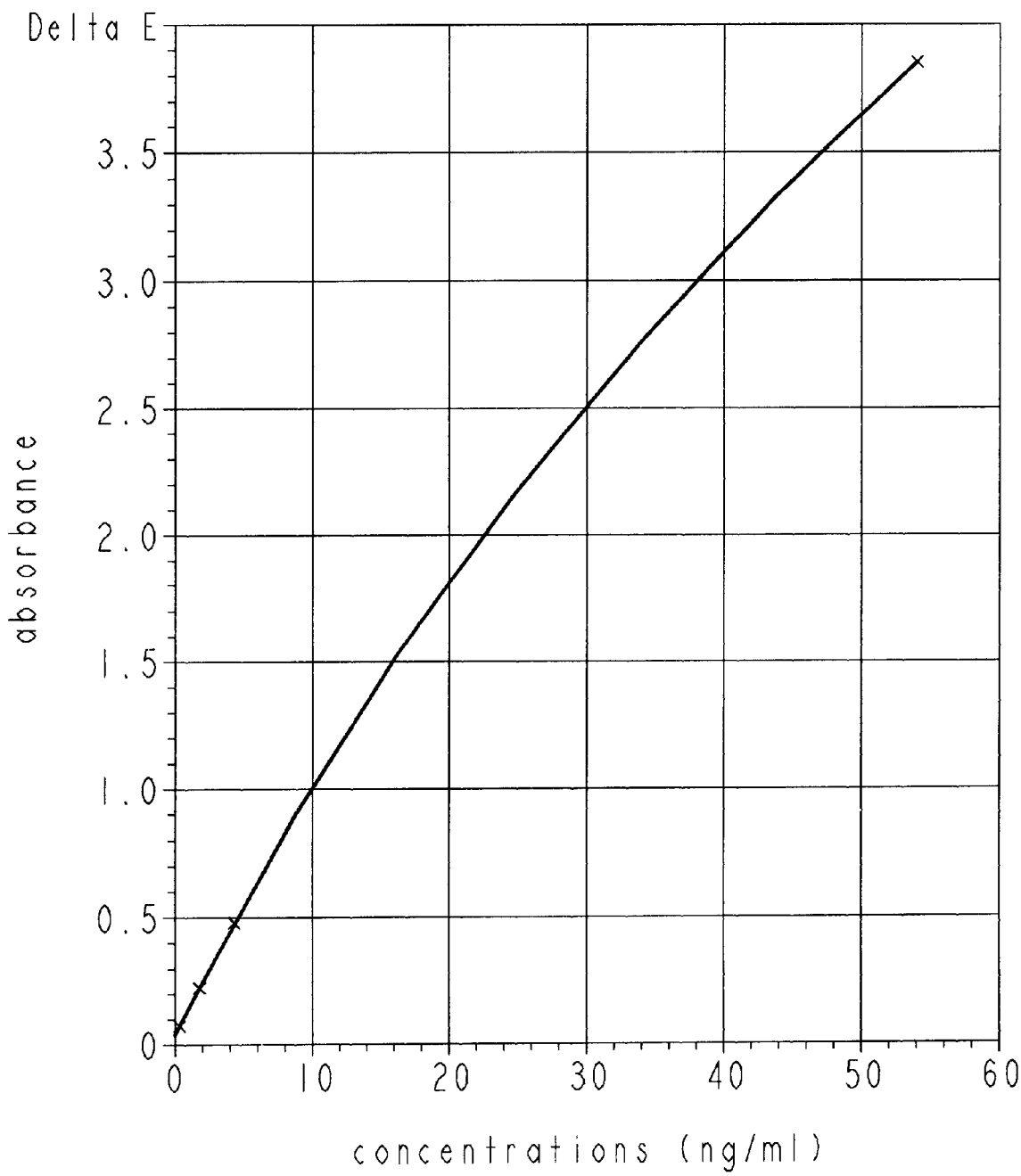
FIG. 1 is a graph showing an enzymun test PSA-ACT complex.

In order to produce serpin-protease receptors, cells are firstly cultured which express the desired receptor. The receptor is for example detected using a cell ELISA as described by Hashemi et al., J. Lab. Clin. Med. 109 (1987), 434–440. For this Hep G2 cells are sown at a density of $2\times10^4$ cells/ml in flat-bottom culture vessels (Costar). DMEM containing 10% foetal calf serum (FCS) is used as the culture medium. The Hep G2 cells are grown up to a 70% total amount and subsequently left unfixed. ACT-PSA (Scripps laboratories) is added to a final concentration of 10 µg/ml in DMEM/1% BSA and allowed to stand for 10 minutes at 4° C. in order to complex with the receptor. After washing twice with DMEM/1% BSA, the cells are incubated for 30 minutes at 4° C. with an anti-PSA monoclonal antibody which is labelled with peroxidase (1 U/ml). Subsequently the cells are washed twice with DMEM/1% BSA. The cells are incubated with substrate (TMB) for the detection.

In order to isolate the receptor, Hep G2 cells which exhibit a high expression of the receptor are cultured in T 150 culture flasks and the cell layers that form are harvested by carefully scraping off the cells. Cells from several culture vessels are pooled in order to obtain a total amount of $10^9$ cells. Subsequently the cells are lysed by incubation with 1% Triton X100 in PBS. After centrifugation at 10,000×g for 10 minutes, the cell culture supernatant is separated and the precipitate containing the nuclear and cell membrane fractions is resuspended in 1 M sodium chloride in PBS. After centrifugation at 10,000×g for 10 minutes, the cell supernatant is collected and stored at −20V C. This receptor preparation can be used to characterize the receptor in ELISA methods. 20 µg of this crude receptor extract is coated for 1 hour at room temperature on flat-bottom microtitre plates. After washing with PBS/0.1% Tween®20 and reloading with PBS/1% BSA, the PSA-ACT complex is added and the mixture is incubated for 1 hour at room temperature. The plates are washed and subsequently incubated with a peroxidase-labelled anti-PSA antibody. The bound peroxidase activity is subsequently detected with a suitable peroxidase colour substrate such as ABTS®.

A hydrophobic chromatography is carried out to further purify the crude receptor extract. The activity of the individual fractions is detected as described above with an ELISA and the fractions with receptor activity are pooled. Afterwards the $NH_2$ terminus of the receptor molecule is sequenced by known methods and the cDNA is fished out of a gene bank. For this purpose the purified receptor preparation is firstly separated by SDS-PAGE. The protein bands are cut out and eluted. The receptor activity of the individual bands is determined by competition using a cell ELISA. The $NH_2$ terminus of the active bands is subsequently sequenced using known methods. The nucleic acid sequence is derived from the amino acid sequence and corresponding oligoprimers are synthesized. A second degenerate primer from the non-translated region before the poly A region is also used for PCR amplification with Hep G2 DNA as the template. Positive clones are identified with the aid of the amplified sequence (ca. 45 nucleotides) and purified. The DNA is characterized by restriction analysis and Southern blots. An EcoRI-XbaI fragment is subcloned into Bluescript SK. The sequence analysis of the clone and the derivation of the amino acid sequence proves the receptor specificity. A DNA which correlates with the receptor sequence is identified with the aid of this oligonucleotide in a cDNA bank for example of foetal liver in λDR2 (Clontech cat. No. HL 1151x). The identified clones are purified and analysed with PCR using primers in the vicinity of the BAMHI-XbaI region in λDR2. The phage suspension is used as a template. The plasmid pDR2 is isolated and subjected to a restriction analysis with BAMHI and XbaI. The double-stranded DNA insert is sequenced with an autosequencer (ABI 373) using standard procedures for colour labelled dideoxynucleoside triphosphate terminators and "walking primers" (Sanger et al., PNAS (1977) 74, 5463–5467).

Afterwards the receptor DNA is isolated and an expression system is constructed. For this the cDNA which contains the open reading frame for the receptor is cloned into the plasmid pSV15.JD.LL between the restriction sites Cla I and Sal I. The vector pSV15.JF.LL.SERC is obtained.

a) Expression in *E. coli*

The plasmid contains a short leader sequence upstream of the receptor gene. This leader sequence allows a high translation rate and a rapid purification. After induction of the tryptophan promoter, a high intracellular production is initiated. The expression plasmid is used to for example transform *E. coli* 44C6 with the aid of the $CaCl_2$ heat shock method according to Mandel et al., J. Mol. Biol. 53 (1970), 159–162. The cells transformed in this manner are allowed to grow at 37° C. in LB medium containing 50 μg/ml carbenicillin up to an optical density of 2–3 at 600 nm. The suspension is diluted 20-fold with M9 medium containing 0.49% casamino acids and 50 μg/ml carbenicillin. They are cultured for a further one hour at 30° C. with aeration and indolyl-3-acrylic acid is added to a final concentration of 50 μg/ml. The cells are harvested after a further culture for 15 hours.

b) Expression in CHO or Other Mammalian Cells

The plasmid is linearized with Not I and CHO cells are transfected by electroporation (Andreason, J. Tissue Culture Meth. 15 (1993), 56). The cells are transferred into DHFR selection medium. After 2 weeks individual clones are transferred to 96-well microtitre plates. The expression is determined by means of a competitive ELISA.

c) The Expression Can Also Take Place in the Baculovirus System According to Known Methods After the receptor has been expressed, it is isolated, purified, characterized and its use as a binding partner in an immunoassay is evaluated. For this the culture supernatant of the transfected CHO cells is collected and applied to a Cibachrome blue-Sepharose column (100 parts by volume cell supernatant/1 part by volume column material). The column is washed with 5 parts by volume application buffer without urea and subsequently washed with 10 mM phosphate buffer pH 7.4 containing 2 M urea (5 parts by volume). The recombinant receptor is eluted with 10 mM phosphate buffer pH 7.4, 2 M urea and 1 M NaCl. The fractions containing receptor are applied to a wheatgerm lectin column. After washing with 5 parts by volume application buffer, the receptor is eluted with 10 mM phosphate buffer pH 7.4, 2 M urea and 0.5 N-acetyl D glucosamine.

The combined fractions containing receptor are adjusted to 0.04% $C_{12}E_8$ and 0.1% TFA. The proteins are separated on a C4 reversed phase column using two consecutive linear acetonitrile gradients (0–30% and 30–60% in 0.04% $C_{12}E_8$ and 0.1% TFA). The fractions are analysed by means of SDS-PAGE. The fractions containing receptor are combined and diluted with 2 volumes of 10 mM sodium phosphate buffer pH 7.4 and 150 mM NaCl and dialysed against 6 volumes of the diluent buffer in an ultrafiltration chamber (exclusion size 30,000) and concentrated.

The concentrate is adjusted to 0.01% TWEEN®80 and purified in the same buffer by means of gel chromatography to remove aggregates and fragments. The fractions containing receptor (detected by SDS-PAGE) are sterile filtered (filter with a pore diameter of 0.22 μm) and stored at 4° C.

The receptor expressed in *E. coli* is isolated as follows. The *E. coli* cells are homogenized in 10 volumes buffer (10 mM Tris-HCl, 5 mM EDTA, pH 8) and centrifuged for 30 minutes at 5000×g. The cells are taken up in 10 volumes of buffer (10 mM Tris-HCl, 5 mM EDTA, pH 8), passed for example through a microfluidizer and centrifuged. The cell pellet is frozen at −70° C. or it is used directly.

The cell pellet is resuspended in 20 mM Tris-HCl, 8 M guanidinium hydrochloride and 25 mM DTT, pH 8 and stirred for 12 hours at 4° C. to solubilize the receptor molecules. After solubilization the solution is centrifuged for 30 minutes at 30,000×g. The clear cell supernatant is isolated and this solution is purified on a G200 Sephadex column (gel chromatography column) in 20 mM Na phosphate buffer containing 10 mM DTT, pH 6. The fractions containing receptor are combined (protein detection by SDS-PAGE). These fractions are separated as described above on a C4 reversed phase column. The fractions containing receptor are again combined and the receptor is renatured. For this the solution is diluted with 9 volumes of renaturation buffer (5 mM EDTA, 2% CHAPS detergent 25% glycerol, 5 mM oxidized glutathione and 1 mM reduced glutathione, pH 8.3) and dialysed for 4 days at 4° C. After renaturation the solution is adjusted to 0.2% TFA, filtered through a 0.45μ filter and adjusted to 10% acetonitrile. This is followed by a C4 reversed phase column as described above. The fractions containing receptor are dialysed against an isotonic buffer (10 mM Na phosphate buffer, 150 mM NaCl and 0.01% Tween®80, pH 7.4) and stored at 4° C.

The cell pellet is resuspended in 20 mM Tris-HCl, 8 M guanidinium hydrochloride and 25 mM DTT, pH 8 and stirred for 12 hours at 4° C. to solubilize the receptor molecules. After solubilization the solution is centrifuged for 30 minutes at 30,000×g. The clear cell supernatant is isolated and this solution is purified on a G200 Sephadex column (gel chromatography column) in 20 mM Na phosphate buffer containing 10 mM DTT, pH 6. The fractions containing receptor are combined (protein detection by SDS-PAGE). These fractions are separated as described above on a C4 reversed phase column. The fractions containing receptor are again combined and the receptor is renatured. For this the solution is diluted with 9 volumes of renatured buffer (5 mM EDTA, 2% CHAPS detergent 25% glycerol, 5 mM oxidized glutathione and 1 mM reduced glutathione, pH 8.3) and dialysed for 4 days at 4° C. After renaturation the solution is adjusted to 0.2% TFA, filtered through a 0.45μ filter and adjusted to 10% acetonitrile. This is followed by a C4 reversed phase column as described above. The fractions containing receptor are dialysed against an isotonic buffer (10 mM Na phosphate buffer, 150 mM NaCl and 0.01% TWEEN®80, pH 7.4) and stored at 4° C.

The tests according to the invention for the detection of PSA-ACT and in particular the one-step test are excellently suitable for screening a large number of samples in order to obtain evidence for the presence of a prostate carcinoma. It has turned out that the use of the test according to the invention enables the cut-off to be lowered compared to the previously common cut-off in tests for the detection of total PSA. Even in ranges below the previously common cut-off values, the test according to the invention still enables a relatively reliable differentiation between normal patients and patients at risk. However, at the same time patients are also detected to an increasing extent which have a prostate carcinoma in an early stage which were not detected by the previously common tests. The cut-off values for the test according to the invention are considerably lower than the corresponding cut-off value for total PSA. The cut-off values for PSA-ACT is ≦70% of the cut-off value for PSA, preferably ≦60% (in ng/ml). At the same specificity (95% against BPH) the cut-off value for total PSA is for example 10.05 ng/ml and the cut-off value for PSA-ACT is 5.70 ng/ml.

In patients which have values that are above the cut-off for this test according to the invention, a second test for the detection of free PSA is carried out to differentiate between benign diseases and prostate carcinomas. Such tests have already been available since 1985. The ratio of free PSA to PSA-ACT is determined. If this ratio is above 0.1 to 0.17 this is a strong indication for the presence of a carcinoma.

The following examples are intended to illustrate the subject matter of the present invention.

EXAMPLE 1

Production of Monoclonal Antibodies to PSA-ACT a) Immunization of Mice 12 week old female Balb/c mice are given a primary intraperitoneal immunization with 100 μg PSA-ACT (Centro Co., San Diego, product code CB 3075-01, batch 50 10 70) together with the adjuvant CFA (complete Freund's adjuvant). This is followed by three further intraperitoneal immunizations after 6 weeks at monthly intervals. In this case each mouse is administered 100 μg PSA-ACT together with IFA (incomplete Freund's adjuvant). Subsequently the last immunizations are carried out intravenously using 100 μg PSA-ACT in PBS buffer on the 3rd and 2nd day and on the last day before fusion.

b) Fusion and Cloning

The spleen cells of the mice immunized according to a) are fused with myeloma cells according to Galfré, Methods in Enzymology 73, 1981, 3. Ca. $1\times10^8$ spleen cells of the immunized mouse are mixed with $2\times10^7$ myeloma cells (P3X63-Ag8-653, ATCC CRL 1580) and centrifuged (10 min at 300 g and 4° C.). The cells are then washed once with RPMI 1640 medium without foetal calf serum (FCS) and again centrifuged at 400 g in a 50 ml conical tube. Subsequently 1 ml PEG (polyethylene glycol) (molecular weight 4000, Merck, Darmstadt) is added and it is mixed by pipetting. After 1 min in a water bath at 37° C., 5 ml RPMI 1640 without FCS is added dropwise, mixed, made up to 50 ml with medium (RPMI 1640+10% FCS) and subsequently centrifuged. The sedimented cells are taken up in RPMI 1640 medium containing 10% FCS and sown in hypoxanthine-azaserine selection medium (100 mmol/l hypoxanthine, 1 μg/ml azaserine in RPMI 1640+10% FCS). Interleukin 6 (100 U/ml) is added to the medium as a growth factor.

After ca. 10 days the primary cultures are tested for specific antibody synthesis (see example 2). Primary cultures which exhibit a positive reaction with PSA-ACT and no cross-reaction with non-complexed PSA and non-complexed ACT or with all other serum components, are cloned in 96-well cell culture plates by means of a fluorescence activated cell sorter. Interleukin 6 (100 U/ml) is added to the medium as a growth additive.

The deposited cell lines/clones listed in table 1 were obtained in this manner.

TABLE 1

| Clone | IgG subclass |
| --- | --- |
| 4.3.2 | IgG1 |
| 6.13.64 | IgG1 |
| 4.6.374 | IgG1 | c) Immunoglobulin Isolation from the Cell Culture Supernatants

The hybridoma cells obtained are sown at a density of $1\times10^5$ cells per ml in RPMI 1640 medium containing 10% FCS and proliferated for 7 days in a fermenter (Thermodux Co., Wertheim/Main, model MCS-104XL, order No. 144-050). Average concentrations of 100 μg monoclonal antibody per ml were reached in the culture supernatant. This antibody is purified from the culture supernatant by common methods in protein chemistry (e.g. according to Methods in Enzymology 121 (1986), 587–695).

EXAMPLE 2

Screening Test for Anti-PSA-ACT Antibodies

Streptavidin-coated MTPs are coated with "capture antibodies" which bind PSA and PSA-ACT. Afterwards they are then incubated with the analyte PSA-ACT (for a)) or PSA (for b)). An incubation is then carried out with the anti-PSA-ACT antibody that is to be tested. Finally the bound antibodies are detected in the usual manner by conversion of a substrate using an anti-mouse IgG-POD.

a) Determination of the Specificity with PSA-ACT

In order to determine the specificity of the antibodies in the culture supernatant of the hybridoma cells, MTPs coated with recombinant streptavidin (MicroCoat Co. Penzberg, order No. 12-K 96 N, batch MC 289) are coated with 10 μg/ml biotinylated Fab fragment of the monoclonal antibody 1 or of the monoclonal antibody 2 (both monoclonal antibodies recognize non-complexed PSA as well as PSA in a complex) in PBS plus 0.5% crotein C (100 μl per well, 10 min incubation at room temperature while shaking) and subsequently washed 3x with 0.9% NaCl/0.05% TWEEN®20).

Afterwards they are incubated with 100 ng/ml PSA-ACT (Scripps Co., San Diego, cat No. p 0624, batch 66 15 64 or Centro Co., San Diego, cat. No. CB 30 75 01, batch 50 10 70) dissolved in PBS plus 0.5% crotein C (100 μl per well, 1 h at room temperature while shaking).Subsequently they are washed 3× with 0.9% NaCl/0.05% TWEEN®20.

In the next step 100 µl of the antibody solution (in the culture supernatant) to be examined is added to a coated well and incubated for 1 hour at room temperature while shaking. After washing 3 times with 0.9% sodium chloride/0.05% TWEEN®20, 100 µl of a POD-labelled Fab fragment of a polyclonal antibody from the sheep against mouse Fcγ (Boehringer Mannheim GmbH, order No. 1431323 corresponding to 25 mU/ml) is added to each well to detect bound antibody from the sample, incubated for 1hour at room temperature while shaking and subsequently washed 3× with 0.9% sodium chloride/0.05% TWEEN®20.

Finally 100 µl/well ABTS® solution (Boehringer Mannheim GmbH, cat. No. 1204521 and 1204530) is added and the absorbance at 405/492 nm is measured after 30 min at room temperature in a MR700 microplate reader from the Dynatech Company.

b) Determination of the Reactivity/cross Reaction with PSA

In order to determine the reactivity/cross reaction with PSA, non-complexed PSA is used in the incubation described under a) instead of PSA-ACT.

For this MTPs coated with recombinant streptavidin (MicroCoat Co. Penzberg, order No. 12-K 96 N, batch MC 289) are coated with 10 µg/ml biotinylated Fab fragment of the monoclonal antibody 1 or of the monoclonal antibody 2 (both monoclonal antibodies recognize non-complexed PSA as well as PSA in a complex) in PBS plus 0.5% crotein C (100 µl per well, 10 min incubation at room temperature while shaking) and subsequently washed 3× with 0.9% NaCl/0.05% TWEEN®20.

Afterwards they are incubated with 50 ng/ml PSA (Scripps Co., San Diego, cat No. P 0714, batch 98 43 64) dissolved in PBS plus 0.5% crotein C (100 µl per well, 1 h at room temperature while shaking). Subsequently they are washed 3× with 0.9% NaCl/0.05% TWEEN®20.

In the next step 100 µl of the antibody solution (in the culture supernatant) to be examined is added to a coated well and incubated for 1 hour at room temperature while shaking. After washing 3 times with 0.9% sodium chloride/0.05% TWEEN®20, 100 µl of a POD-labelled Fab fragment of a polyclonal antibody from the sheep against mouse Fcγ (Boehringer Mannheim GmbH, order No. 1431323 corresponding to 25 mU/ml) is added to each well to detect bound antibody from the sample, incubated for 1 hour at room temperature while shaking and subsequently washed 3× with 0.9% NaCl/0.05% TWEEN®20.

Finally 100 µl/well ABTS® solution (Boehringer Mannheim GmbH, cat. No. 1204521 and 1204530) is added and the absorbance at 405/492 nm is measured after 30 min at room temperature in a MR700 microplate reader from the Dynatech Company.

c) Determination of the Reactivity with ACT

In order to determine the reactivity with ACT the antibody to be examined is preincubated with ACT in excess in the test described under a). If the level of the measured signal remains unchanged, there is no cross-reaction, if the measured signal is decreased then a cross-reaction is present.

For this MTPs coated with recombinant streptavidin (MicroCoat Co. Penhzberg, order No. 12-K 96 N, batch MC289) are coated with 10 µg/ml biotinylated Fab fragment of the monoclonal antibody 1 or of the monoclonal antibody 2 (both monoclonal antibodies recognize non-complexed PSA as well as PSA in a complex) in PBS plus 0.5% crotein C (100 µl per well, 10 min incubation at room temperature while shaking) and subsequently washed 3× with 0.9% NaCl/0.05% TWEEN®20.

Afterwards they are incubated with 100 ng/ml PSA-ACT (Scripps Co. or Centro Co.) dissolved in PBS plus 0.5% crotein C (100 µl per well, 1 hour at room temperature while shaking). Subsequently they are washed 3× with 0.9% NaCl/0.05% TWEEN®20.

The antibody that is to be tested for cross-reaction is preincubated in a concentration series of 0, 10 µg, 50 µg, 100 µg/ml ACT (Athens Co., Athens, order No. 16-16-012400, batch AX9501). The preincubation is carried out in uncoated 96-well MTP wells for 1 h at room temperature while shaking.

In the next step 100 µl of this solution (antibody+ACT in excess) is added to a coated well and incubated for 1 hour at room temperature while shaking. After washing 3 times with 0.9% sodium chloride/0.05% Tween®20, 100 µl of a POD-labelled Fab fragment of a polyclonal antibody from the sheep against mouse Fcγ (Boehringer Mannheim GmbH, order No. 1431323 corresponding to 25 mU/ml) is added to each well to detect bound antibody from the sample, incubated for 1 hour at room temperature while shaking and subsequently washed 3× with 0.9% sodium chloride/0.05% Tween®20.

Finally 100 µl/well ABTS® solution (Boehringer Mannheim GmbH, cat. No. 1204521 and 1204530) is added and the absorbance at 405/492 nm is measured after 30 min at room temperature in a MR700 microplate reader from the Dynatech Company.

d) Determination of the Reactivity with Other Serum Components

In order to determine the reactivity with other serum components the antibody to be examined is preincubated with human, female serum in the test described under a). If the level of the measured signal remains unchanged, there is no cross-reaction, if the measured signal is decreased then a cross-reaction is present.

In the next step 100 µl of this solution (antibody+ACT in excess) is added to a coated well and incubated for 1 hour at room temperature while shaking. After washing 3 times with 0.9% sodium chloride/0.05% TWEEN®20, 100 µl of a POD-labelled Fab fragment of a polyclonal antibody from the sheep against mouse Fcγ (Boehringer Mannheim GmbH, order No. 1431323 corresponding to 25 mU/ml) is added to each well to detect bound antibody from the sample, incubated for 1 hour at room temperature while shaking and subsequently washed 3× with 0.9% sodium chloride/0.05% TWEEN®20.

Afterwards they are incubated with 100 ng/ml PSA-ACT (Scripps Co. or Centro Co.) dissolved in PBS plus 0.5% crotein C (100 µl per well, 1 hour at room temperature while shaking). Subsequently they are washed 3× with 0.9% NaCl/0.05% TWEEN®20.

The antibody that is to be tested for cross-reaction is preincubated in a concentration series (1:1 to 1:10) of human, female sera (a mixture of four PSA-negative female donors). The preincubation is carried out in uncoated 96-well MTP wells for 1 h at room temperature while shaking.

In the next step 100 µl of this solution (antibody+female human serum) is added to a coated well and incubated for 1 hour at room temperature while shaking. After washing 3 times with 0.9% sodium chloride/0.05% TWEEN®20, 100 µl of a POD-labelled Fab fragment of a polyclonal antibody from the sheep against mouse Fcγ (Boehringer Mannheim GmbH, order No. 1431323corresponding to 25 mU/ml) is added to each well to detect bound antibody from the sample, incubated for 1 hour at room temperature while shaking and subsequently washed 3× with 0.9% sodium chloride/0.05% Tween®20.

Finally 100 μl/well ABTS® solution (Boehringer Mannheim GmbH, cat. No. 1204521 and 1204530) is added and the absorbance at 405/492 nm is measured after 30 min at room temperature in a MR700 microplate reader from the Dynatech Company.

All deposited monoclonal antibodies exhibited a strong reactivity with PSA-ACT. A clinically relevant reactivity with PSA, ACT and other serum components was not detectable with these test methods using any of the deposited monoclonal antibodies. The deposited, monoclonal antibodies were found in a screening of several thousand monoclonal antibodies of which ca. 70% cross-reacted strongly with ACT and ca. 30% cross-reacted strongly with PSA.

EXAMPLE 3

Determination of the Affinity Constants and the Rate Constants of Association and Dissociation of the Produced Antibodies The affinity constants and the rate constants of the association and dissociation of the produced antibodies were determined using BIACORE® from the Pharmacia Biosensor Company (BIA stands for biospecific interaction analysis). The measurement principle is based on surface plasmon resonance. The measurement is carried out on a biosensor, the so-called sensor chip. In this process a polyclonal rabbit antibody against the Fcγ part of mouse IgG is covalently coupled via its amino groups onto the surface of a sensor chip (CM5, Pharmacia Biosensor) coated with carboxymethylated dextran. A solution of the antibody to be determined is passed over this sensor chip during which the antibody is bound to the immobilized capture antibody by means of non-covalent interaction forces. Subsequently the antigen to be examined is passed over the sensor chip which is then also bound by means of non-covalent interaction forces to the antibody immobilized by the capture antibody.

The binding of the individual components increases the mass density on the surface of the sensor chip which is converted by the instrument into a proportional measurement signal. The change in the signal versus time, the sensorgraph, allows a calculation of the rate constants of association and dissociation and from these the affinity constant.

The antibody-antigen complexes can be detached again by simple means without impairing the capture antibodies bound to the surface so that further binding experiments can be carried out on the same sensor chip under identical boundary conditions.

In order to couple the capture antibody to the sensor chip (CM5, Pharmacia Biosensor) a solution of the antibody (BIA certified rabbit anti-mouse Fcγ, Pharmacia Biosensor) at a concentration of 60 μg/ml in 10 mM sodium acetate buffer pH 5.0 is passed at a flow rate of 5 μl/min over the sensor chip previously activated with NHS/EDC.

Afterwards the antibodies are added so that an increase in the mass bound to the surface of at least 600 resonance units occurs. The binding of the antigens to the antibodies is monitored at a flow rate of 10 μl/min and the rate constants of association and dissociation for the binding of the antibody is calculated from the sensorgraphs with the aid of the manufacturer's software (BIAevaluation 2.1, Pharmacia Biosensor). The affinity constants are calculated from $K_a = k_{on}/k_{off}$. The values determined in this manner for the antibody according to the invention with PSA-ACT, chymotrypsin-ACT and cathepsinG-ACT as antigens are summarized in the following table 2. No binding can be detected with non-complexed PSA, chymotrypsin, cathepsin G as well as with free human ACT as an antigen i.e. the affinity constants for these compounds is less than $10^5$ l/mol.

TABLE 2

| | PSA-ACT | | | chymotrypsin-ACT | | | cathepsin-G-ACT | | |
|---|---|---|---|---|---|---|---|---|---|
| clone | kon 1/mol*s | koff 1/s | ka 1/mol | kon 1/mol*s | koff 1/s | ka 1/mol | kon 1/mol*s | koff 1/s | ka 1/mol |
| 4.6.374 | $1*10^5$ | $1*10^{-5}$ | $1*10^{10}$ | $1*10^5$ | $3*10^{-4}$ | $3*10^8$ | $1*10^5$ | $5*10^{-5}$ | $2*10^8$ |
| 4.3.2 | $3*10^4$ | $9*10^{-4}$ | $4*10^7$ | $8*10^4$ | $3*10^{-3}$ | $3*10^7$ | $1*10^5$ | $1*10^{-3}$ | $9*10^7$ |
| 6.13.64 | $5*10^4$ | $2*10^{-3}$ | $2*10^7$ | $1*10^5$ | $3*10^{-3}$ | $3*10^7$ | $1*10^5$ | $2*10^{-3}$ | $8*10^7$ |
| 4.1.358 | $5*10^4$ | $6*10^{-3}$ | $9*10^6$ | $5*10^4$ | $6*10^{-3}$ | $9*10^6$ | $8*10^4$ | $2*10^{-3}$ | $5*10^7$ |
| 4.9.358 | $5*10^4$ | $6*10^{-3}$ | $9*10^6$ | $5*10^4$ | $6*10^{-3}$ | $9*10^6$ | $8*10^4$ | $2*10^{-3}$ | $4*10^7$ |

EXAMPLE 4

Screening to Detect a Suspected Prostate Carcinoma a) Screening Test

Groups of 276 healthy men, 456 patients with benign prostate hyperplasia (BPH) and 348 patients with proven prostate carcinoma (PCa) were examined.

The total PSA in the serum was determined with the Enzymun test PSA. In addition PSA-ACT was measured by substituting the detection antibody of the Enzymun test® PSA by the antibody 4.6.374 specific for PSA-ACT (after POD labelling) and otherwise the procedure was according to the instructions of the package insert.

b) Result

The distribution of the PSA values in the three groups is shown in table 3. 90% of the healthy persons, 38% of the BPH patients and 16% of the carcinoma patients were below the usual cut-off value of 4 ng PSA/ml. Test persons whose PSA value was above the cut-off are examined further; whereas those whose PSA concentration was below the decision value were regarded as having a healthy prostate.

If instead of 4 ng/ml PSA, a limit of 3 ng/ml PSA-ACT is used, then again 90% of the healthy persons are below this value whereas in this case three additional prostate carcinoma patients are correctly identified (see table 4).

Hence by substituting the screening parameter a higher sensitivity was achieved in the carcinoma group with the same specificity with regard to a normal group.

50 µl serum sample or PSA-ACT standard was incubated for 1 hour with 700 µl reagent 1 (40 mmol/l sodium phosphate buffer, pH 7.4/0.2% (w/v) bovine serum albumin/ 1.2 µg/ml biotinylated monoclonal anti-PSA antibody M10, Fab fragment, in streptavidin-coated ENZYMUN® universal tubes and subsequently washed.

TABLE 3

Cut-off: PSA 4 ng/ml

|  | Healthy | BPH | PCa |
|---|---|---|---|
| Total number of values number of values in the range | 276 | 456 | 348 |
| PSA ≦ 4 ng/ml | 249 | 174 | 54 |
| PSA > 4 ng/ml | 27 | 282 | 294 |
| percentage (%) of values in the range |  |  |  |
| PSA ≦ 4 ng/ml | 90.2 | 38.2 | 15.5 |
| PSA > 4 ng/ml | 9.8 | 61.8 | 84.5 |

TABLE 4

Cut-off: PSA-ACT 3 ng/ml

|  | Healthy | BPH | PCa |
|---|---|---|---|
| Total number of values numbers of values in the range | 276 | 456 | 348 |
| PSA ≦ 3 ng/ml | 248 | 158 | 51 |
| PSA > 3 ng/ml | 28 | 298 | 297 |
| percentage (%) of values in the range |  |  |  |
| PSA ≦ 3 ng/ml | 89.9 | 34.6 | 14.7 |
| PSA > 3 ng/ml | 10.1 | 65.4 | 85.3 |

EXAMPLE 5

Immunoassay for the Determination of PSA-ACT a) Immunoassay Procedure on an ES 300 (Boehringer Mannheim GmbH)

50 µl serum sample or PSA-ACT standard was incubated for 1 hour with 700 µl reagent 1 (40 mmol/l sodium phosphate buffer, pH 7.4/0.2% (w/v) bovine serum albumin/ 1.2 µg/ml biotinylated monoclonal anti-PSA antibody M10, Fab fragment, in streptavidin-coated Enzymun® universal tubes and subsequently washed.

Afterwards 700 µl reagent 2 (40 mmol/l sodium phosphate buffer, pH 7.4/0.2% (w/v) bovine serum albumin/0.1% bovine IgG/monoclonal anti-PSA-ACT antibody, clone 4.6.374, (Fab)$_2$'-POD conjugate, 95 mU/ml) was added and washed after 30 min incubation.

The colour was developed for 30 min using 700 µl substrate solution (1 mg/ml ABTS®/0.5 mg/ml sodium perborate/citrate/phosphate buffer) and was measured at 422 nm in a photometer.

FIG. 1 shows a typical calibration curve.

b) Relevant Cross-reactions in the Test

A female serum in which no endogenous PSA was measurable was used as a sample in the test system described under a). Purified ACT (Serva Co.) or chymotrypsin-ACT complex (50 µg/ml in each case) were added to separate aliquots of this serum. The same additions were also made to a human serum with an elevated endogenous PSA content. In addition a solution of 22 ng/ml free PSA in phosphate buffer was used in the test instead of serum.

The measured PSA-ACT contents in these samples are shown in table 5. The measured cross-reactions for PSA and ACT in the test were in all cases <0.003% and none of the added materials led to a PSA-ACT result which falsified the assessment of the sample.

c) Measurement of Sera from Healthy Women and From Women with Various Inflammations The PSA-ACT concentrations were measured in 40 sera of healthy women and in 18 sera from female patients with various inflammations using the test described under a). In the first group the PSA-ACT level was on average 0.01 ng/ml (±0.03 ng/ml standard deviation) whereas in the inflammation group an average of 0.03 (±0.04) ng PSA-ACT/ml was found.

This shows that other ACT complexes, e.g. the cathepsin G-ACT increased in inflammations, or other naturally occurring ACT-protease complexes do not lead to interference with the test.

TABLE 5

| Sample | PSA-ACT measured [ng/ml] | Cross-reaction in the test |
|---|---|---|
| human serum, PSA-free |  |  |
| without addition + | 0 |  |
| ACT [50 µg/ml] + | 0 | 0 |
| chymotrypsin-ACT [50 µg/ml] | 0.13 | 0.0003% |
| human serum, untreated |  |  |
| without addition + | 41.7 |  |
| ACT [50 µg/ml] + | 43.0 | 0.0026% |
| chymotrypsin-ACT [50 µg/ml] | 42.0 | 0.0020% |
| free PSA in buffer [22 µg/ml] | 0 | 0 |

EXAMPLE 6

Sensitivity and Specificity of the Identification of Prostate Carcinoma

In a group of 48 sera of patients with benign prostate hyperplasia (BPH) and of 45 patients with prostate carcinoma, tPSA and fPSA were determined using the respective Enzymun® tests and PSA-ACT was determined according to example 5. In both groups the PSA content was below 20 ng/ml. In order to obtain information on the discrimination between prostate carcinoma and BPH, and ROC evaluation was carried out (Zweig, M. H., Clin. Chem. 39 (1993) 561–577: "Receiver-operating Characteristic (ROC) Plots: A Fundamental Tool in Clinical Medicine") and the corresponding values for sensitivity and specificity were read off the respective curves. In addition the area under the ROC curve was calculated which is a measure of the ability of a parameter to discriminate between the corresponding tumour group and benign disease group. The larger this area is, the more probable is a correct classification of an unknown sample.

TABLE 6

Result of the ROC evaluation

| Parameter | Area under the curve | Sensitivity (%) at a specificity of 95% |
|---|---|---|
| tPSA | 0.709 | 29 |
| PSA-ACT | 0.748 | 40 |
| fPSA | 0.438 | 9 |

ROC evaluation in the range 0–20 ng PSA/ml

BPH: n=48, PCa: n=45

The sensitivity of prostate carcinoma detection compared to benign prostate hyperplasia was 40% when measuring PSA-ACT compared to 29% for tPSA at the same specificity of 95%. The area under the curve also increased from 0.709 to 0.748 if PSA-ACT is considered instead of tPSA.

Measurement of free PSA as the sole parameter appears to be inappropriate due to the low sensitivity. The area under the fPSA curve was also considerably lower than those of the two other parameters.

EXAMPLE 7

Correlation of Calculated and Measured PSA-ACT Values

Under the assumption that the immunologically measurable total PSA is composed of the two main components fPSA and PSA-ACT, the third parameter can be calculated after measuring the first two parameters and this result is compared to the measured values of the $3^{rd}$ parameter. After determining tPSA and fPSA using the appropriate ENZYMUN® tests, their difference was calculated and the correlation to PSA-ACT measured according to example 5 was determined.

TABLE 7

| Parameter 1 | Parameter 2 | group | number of samples | correlation r |
|---|---|---|---|---|
| PSA-ACT (=Y value) | tPSA- fPSA (=X value) | all samples | 264 | 0.974 |
| | | control, male | 70 | 0.965 |
| | | BPH | 51 | 0.947 |
| | | PCa | 60 | 0.967 |
| | | other diseases male patients | 83 | 0.993 |

Correlation of the measured and calculated PSA-ACT content

The measured and calculated PSA-ACT content correlated very well with r=0.974 over all 264 values and was always greater than 0.946 in individual groups. This shows that the PSA-ACT test with the new monoclonal antibody gives a very plausible result.

What is claimed is:

1. Monoclonal antibodies produced by one of the cell lines MAK<PSA-ACT>M 4.6.374, MAK<PSA-ACT>M 4.3.2 or MAK<PSA-ACT>M 6.13.64 with the depository numbers DSM ACC 2281, DSM ACC 2283 and DSM ACC 2282, respectively.

* * * * *

UNITED STATES PATENT AND TRADEMARK OFFICE
CERTIFICATE OF CORRECTION

PATENT NO.   : 6,630,350 B1
DATED        : October 7, 2003
INVENTOR(S)  : Hubner-Parajsz et al.

It is certified that error appears in the above-identified patent and that said Letters Patent is hereby corrected as shown below:

Title page,
Item [30], Foreign Application Priority Data, delete "Oct. 6, 1996", and insert therefor -- Oct. 9, 1996 --.

Signed and Sealed this

Thirteenth Day of July, 2004

JON W. DUDAS
*Acting Director of the United States Patent and Trademark Office*